United States Patent
Owen et al.

[11] Patent Number: 6,023,980
[45] Date of Patent: Feb. 15, 2000

[54] HIGH-CYCLE FATIGUE TEST MACHINE

[75] Inventors: Thomas E. Owen, Helotes; David L. Davidson; Andrew Nagy, both of San Antonio, all of Tex.

[73] Assignee: Southwest Research Institute, San Antonio, Tex.

[21] Appl. No.: 09/115,116

[22] Filed: Jul. 14, 1998

Related U.S. Application Data

[63] Continuation-in-part of application No. 08/884,594, Jun. 27, 1997, abandoned.
[60] Provisional application No. 60/038,465, Feb. 21, 1997.

[51] Int. Cl.[7] ................................................. G01N 3/00
[52] U.S. Cl. ................................................. 73/797; 73/808
[58] Field of Search .......................... 73/797, 798, 796, 73/856, 857, 860, 808

[56] References Cited

U.S. PATENT DOCUMENTS

| | | | |
|---|---|---|---|
| 2,788,659 | 4/1957 | Radnar et al. | 73/67.4 |
| 3,269,175 | 8/1966 | Sprosty | 73/141 |
| 3,470,400 | 9/1969 | Weisbord | 310/19 |
| 3,479,536 | 11/1969 | Norris | 310/8.5 |
| 3,563,086 | 2/1971 | Reed | 73/92 |
| 3,690,162 | 9/1972 | Stecher | 73/797 |
| 4,355,538 | 10/1982 | Hall | 73/811 |
| 4,372,173 | 2/1983 | EerNisse | 73/862.59 |
| 4,523,121 | 6/1985 | Takahashi et al. | 310/334 |
| 4,546,658 | 10/1985 | Rocha et al. | 73/862.59 |
| 4,637,259 | 1/1987 | Jones | 73/794 |
| 4,667,127 | 5/1987 | Krempl et al. | 310/338 |
| 4,686,860 | 8/1987 | Liu | 73/856 |
| 4,748,854 | 6/1988 | Rao | 73/799 |
| 4,869,111 | 9/1989 | Ohya et al. | 73/811 |
| 4,869,112 | 9/1989 | Gram et al. | 73/796 |
| 5,388,464 | 2/1995 | Maddison | 73/856 |
| 5,425,276 | 6/1995 | Gram et al. | 73/816 |
| 5,442,964 | 8/1995 | Coates et al. | 73/862.68 |
| 5,528,942 | 6/1996 | Baratta | 73/856 |
| 5,581,040 | 12/1996 | Lin | 73/856 |

FOREIGN PATENT DOCUMENTS

| | | |
|---|---|---|
| 3818831 | 12/1989 | Germany . |
| 2137024 | 9/1984 | United Kingdom . |

OTHER PUBLICATIONS

SwRI Proposal for Damage Mechanisms in High Cycle Fatigue, David L. Davidson, Nov. 10, 1995.
SwRI Proposal No. 06–18521 for High Cycle Fatigue of Turbine Engine Materials, S.J. Hudak, Jr., and R.C. McClung, Sep. 27, 1995.
Lee, et al., "Electrohydrolic Fatigue Apparatus for Testing in Ultrahigh Vacuum and Controlled Environments", Review of Scientific Instruments, vol. 57, No. 11, Nov. 1986.
Hoffelner, "Fatigue Crack Growth at 20 kHz—A New Technigue", Journal of Physics, vol. 37, No. 6, Jun., 1990.

*Primary Examiner*—Max Noori
*Attorney, Agent, or Firm*—Baker & Botts, L.L.P.

[57] ABSTRACT

A test machine (10, 40, 60) for inducing high-cycle fatigue (at kilohertz vibration rates) in a specimen of a material under test. Each test machine (10, 40, 60) provides both dynamic and static loading. One embodiment is an SEM-compatible machine (10), having an inner frame (11) containing symmetrical components on either side of a stationary node. The specimen is placed at this stationary vibration node. Dynamic loading is the result of vibrations provided by two piezoelectric actuators (16) inside the frame (11), one on each side of the node. Static loading is provided by means of two stress rods (12), each extending from an end plate (11a) into the frame (11). A pair of cylindrical couplers (14) is also inside the frame, one coupler (14) on each side of the node. Each coupler (14) is attached to an associated piezoelectric actuator (16) and stress rod (12) such that the static and dynamic loads are transferred to the couplers (14). The specimen is held between the inner faces of each coupler 14 such that the loading is transferred to the specimen. The static and dynamic loading applied to the specimen are independent of each other and separately controllable.

27 Claims, 5 Drawing Sheets

HIGH-CYCLE FATIGUE TEST MACHINE

CROSS-REFERENCE TO RELATED APPLICATION

This application is a continuation-in-part of U.S. patent application Ser. No. 08/884,594, filed Jun. 27, 1997, now abandoned, by Thomas E. Owen, et. al., and entitled "High-Cycle Fatigue Test Machine", which claims priority under 35 U.S.C. § 119(c)(1) of provisional application number 60/038,465, filed Feb. 21, 1997.

TECHNICAL FIELD OF THE INVENTION

The present invention relates generally to equipment for testing physical characteristics of materials, and more specifically, to a test machine that subjects a sample of material to high-cycle stress.

BACKGROUND OF THE INVENTION

The study of fatigue in materials calls for stressing the material in question in a manner similar to the conditions encountered in its operating environment. Fatigue resulting from the stress occurs as surface changes such as grain interface deformations, surface microcrack initiation, and the growth of small cracks.

Cyclic stresses affect different materials in different ways, particularly in the presence of other operating environmental conditions such as temperature extremes. High-performance materials, such as metal alloy matrix materials or metal-ceramic matrix materials, tend to have good resistance to cyclic fatigue as well as to high temperatures and high loading stresses. However, the complexity of such materials requires that their performance characteristics be studied experimentally to establish their practical design and fatigue endurance limits.

Conventional equipment for subjecting a material to cyclic stress has provided a vibration frequency (cyclic stress rate) that is either too low or too high (ultrasonic). In the case of a stress rate that is too low, excessive testing time is required to accumulate a desired number of vibration cycles, which may be as many as several million or a billion vibration cycles. In the case of a stress rate that is too high, the result is unrepresentative physical effects in the materials, such as excessive internal friction and self-heating. For example, present-day stress-strain testing machines are not capable of cyclic stress rates above about 100 Hz, and ultrasonic tests are typically performed at 20,000 Hz. However, turbine engine blades experience vibration rates in the range of 1,000 to 4,000 Hz. Thus, cyclic fatigue effects in most materials have not been studied at cyclic stress rates that are characteristic of the application for which the material is used.

Furthermore, a complete study of fatigue effects in materials requires that fatigue-causing dynamic stresses be simultaneously superimposed on static loading conditions. This capability is practical in present-day low-frequency machines but has not been implemented in ultrasonic machines.

Also, cyclic fatigue is a progressive mode of failure in many materials, requiring that the surface of the test specimen be examined periodically to observe incremental changes. In this regard, there is experimental evidence that intermittent sequences of cyclic loading interspersed with low-load static quiescence, as well as the time duration of each of the loading and quiescent states, has an influence on the fatigue-induced defects and the fatigue life of many materials. Therefore, examination of a test specimen immediately after a cyclic stress sequence (and, ultimately, during cyclic loading) is an important requirement in fully understanding the characteristics of material fatigue. Conventional testing machines are not designed to be integrated with specimen inspection systems such as a scanning electron microscope (SEM) or a high magnification metallurgical microscope. As a consequence, the stress-inducing process and the specimen-inspecting process are separated. This separation could cause important fatigue effects to be missed because of the time required to dismount and install the specimens in different test setups.

SUMMARY OF THE INVENTION

One aspect of the invention is a test machine for inducing high-cycle fatigue effects in material test specimens. An inner frame is comprised of two end plates connected by a number of coupling rods aligned along a horizontal axis. A set of bellows is attached to each end plate, each of said bellows having an axis of motion parallel to the horizontal axis of the inner frame. The bellows extend outwardly from the outer surfaces of the end plates and terminate at bearing plates, one at each end of the test machine. Thus, the bellows are interposed between the end plates and bearing plates so that when filled with hydraulic fluid, the bellows may exert force against an end plate and a bearing plate. An axially oriented stress rod is attached to each bearing plate and extends inside the inner frame through clearance holes in each end plate of the inner frame. The stress rods support symmetrically opposing piezoelectric actuators and cylindrical couplers, one actuator and one coupler being on either side of a stationary vibration node inside the inner frame at the midpoint of the horizontal axis.

Each cylindrical coupler has an inner face with means for attaching one end of the test specimen. Each cylindrical coupler is attached to its associated stress rod and its associated piezoelectric actuator, such that static force applied to the stress rod and dynamic force produced by the piezoelectric actuators are both transferred to the specimen.

This test machine overcomes several shortcomings of present-day test machines. The test machine provides cyclic stress rates that have a frequency range of 1000 to 4000 Hz, a range not previously available for stress testing. This frequency range produces cyclic stresses at rates reasonably representative of in-service conditions rather than at the excessively low or high cyclic stress rates provided by previous test equipment. Also, the machine of the present invention is capable of simultaneously subjecting a test specimen to independently controlled static and dynamic loading.

The test machine can be implemented to accommodate two different categories of testing. A first embodiment is an SEM-compatible test machine and a second embodiment is a laboratory test machine. Although each of these embodiments operates under the same basic principle (using the natural resonance of the test machine) for dynamic loading, they implement static loading differently.

The SEM-compatible test machine accommodates the investigation of fatigue effects when the test specimens can be relatively small but examination of the specimen during testing must provide maximum observational detail. The SEM test machine accommodates the need to isolate the vibrations of the test machine from the SEM to avoid vibration interference in the SEM during testing.

The laboratory test machine accommodates the investigation of fatigue effects when less detailed examination is required although periodic microscopic inspection is still needed. It more readily permits testing with high-cycle stress combined with other environmental operating conditions. In general, larger test specimens and larger attendant loading forces are possible using the laboratory test machine, so as to better characterize the bulk material tolerances under cyclic loading.

DETAILED DESCRIPTION OF THE INVENTION

The invention described herein is directed to a stress/strain test machine that satisfies the requirements for the study of high-cycle fatigue in materials. The test specimen can be simultaneously subjected to a static loading force and a cyclic dynamic loading force. The frequency range of the dynamic loading force is 1,000 to 4,000 Hz. During testing, the specimen is accessible for inspection so that progressive fatigue effects can be easily observed by a microscope, such as an SEM (scanning electron microscope) or metallurgical microscope.

One embodiment of the invention is an SEM-compatible test machine, which is sufficiently small to fit and operate inside the vacuum chamber of an SEM. This test machine is within size and weight constraints of about 3.75×4.0×10.5 inches in envelope volume and about 15 pounds in weight. It uses test specimens having a rectangular or cylindrical cross-section in the range of 0.01 to 0.04 square inch and a length of about 0.75 to 1.0 inch, which is a practical size for fatigue studies requiring SEM inspection. The SEM-compatible test machine is configured to permit direct observation of specimens by the SEM during testing.

An alternative embodiment to the SEM-compatible test machine is a larger 'laboratory' test machine. This laboratory test machine satisfies the requirements for studying high-cycle fatigue when a laboratory microscope is sufficient to examine the specimen. In this case, larger test specimens are practical and typically have cross-sectional areas in the range of 0.10 to 0.20 square inch and lengths in the range of 2 to 3 inches. The laboratory test machine is not necessarily constrained in size or weight. However, as will be made clear in the following description, to provide cyclic stress rates in the kilohertz frequency range, the laboratory test machine is inherently smaller than present-day conventional stress/strain testing machines.

The SEM test machine and the laboratory test machine operate on the same basic principle for inducing fatigue caused by dynamic loading. Specifically, both use piezoelectrical means to activate the natural mechanical resonance of the specimen and the test machine. For inducing fatigue caused by static loading, the SEM-compatible test machine uses hydraulic loading means, although, as will be explained in the following description, pneumatic or piezoelectric loading may also be used. The laboratory test machine uses electromechanical means for inducing static loading.

Figure 1:
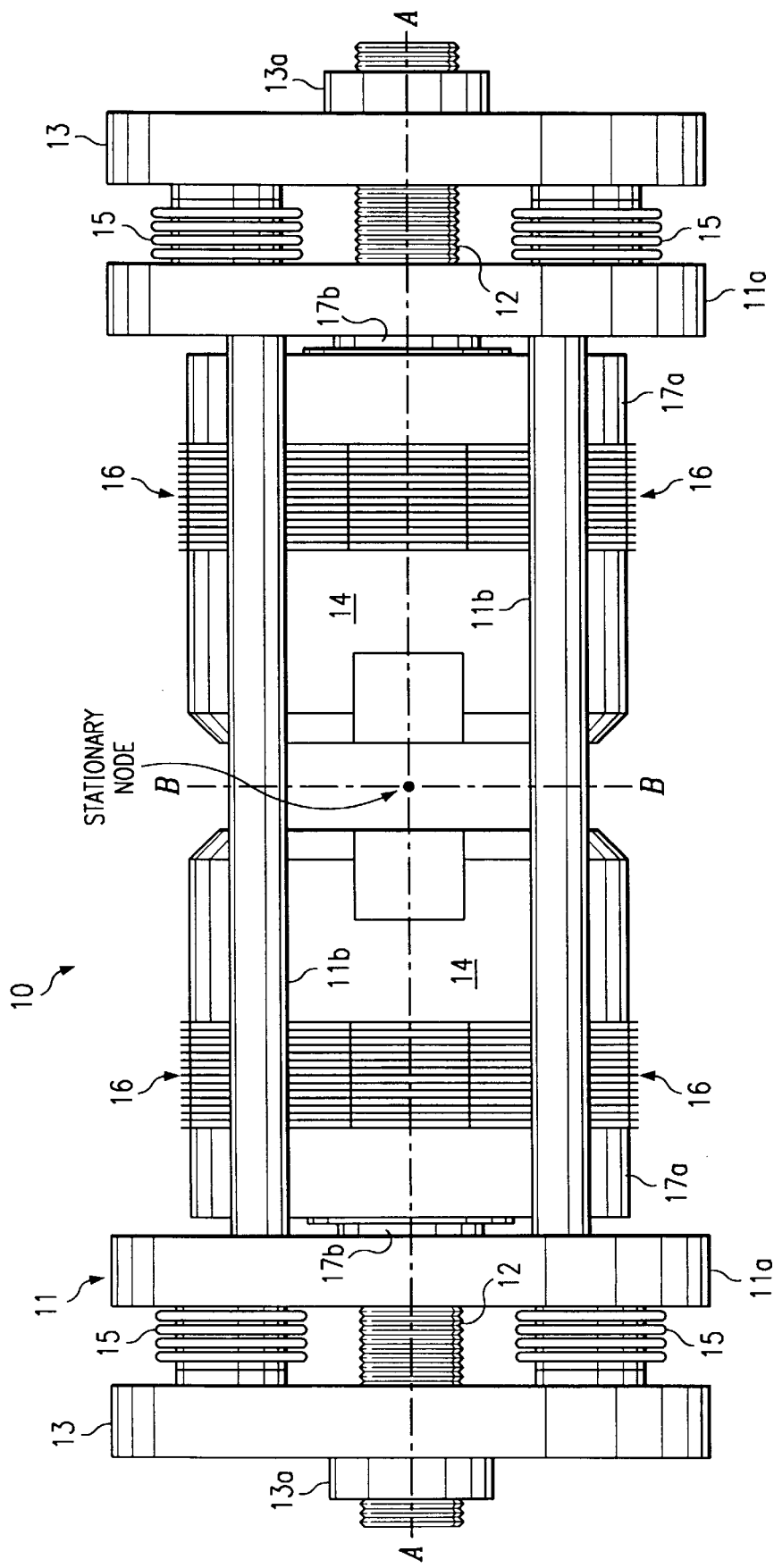
FIG. 1 illustrates an SEM-compatible test machine in accordance with the invention.
Figure 2:
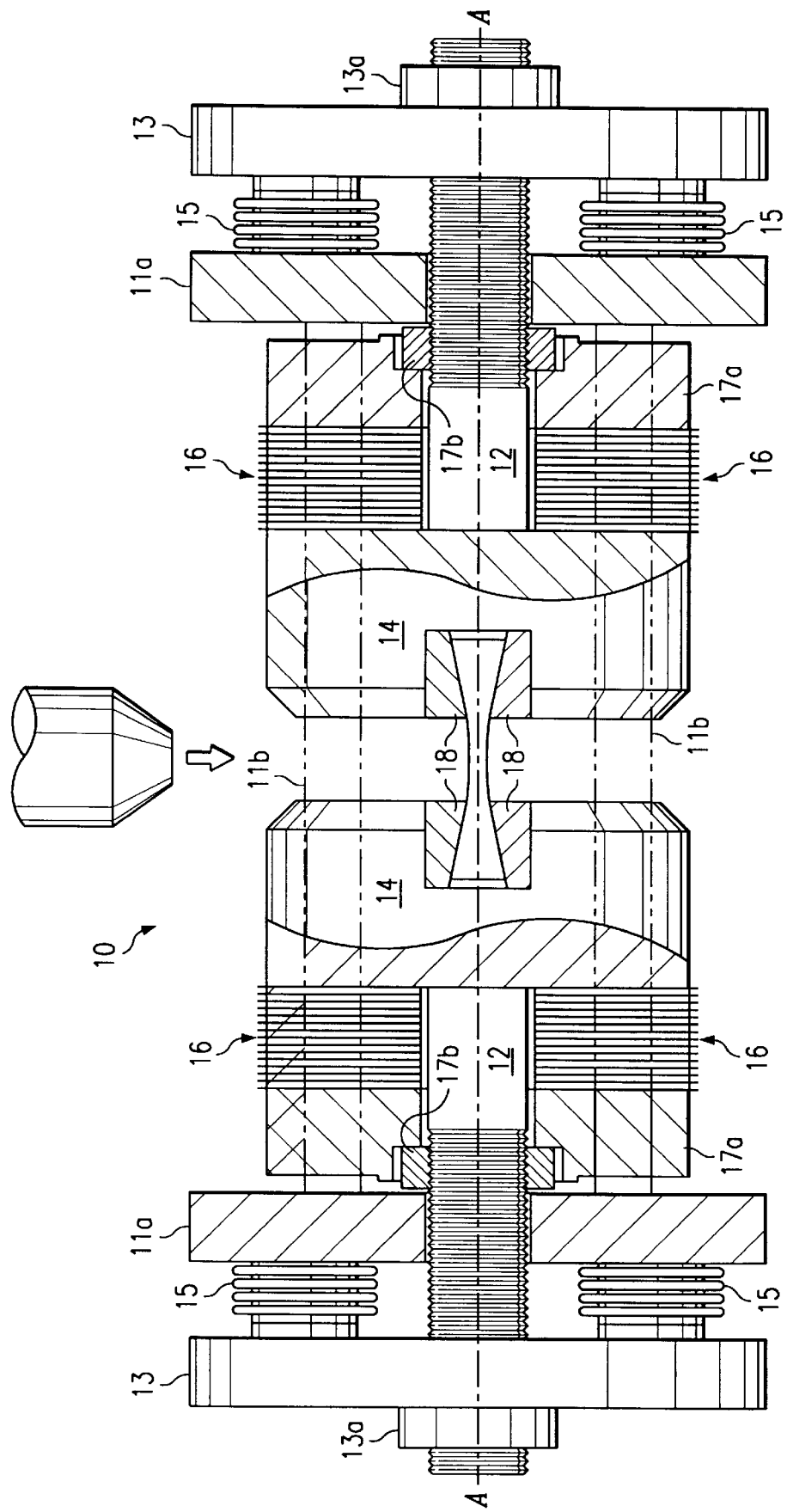
FIG. 2 is a cross-sectional view of the test machine of FIG. 1.

FIG. 1 illustrates the basic elements of an SEM-compatible test machine 10 in accordance with the invention. FIG. 2 is a cross sectional view along axis A—A of FIG. 1. FIG. 2 further illustrates the position of test machine 10 with respect to the SEM field-of-view, as well as the location of a test specimen within test machine 10.

Test machine 10 has various "structural elements", such as an inner frame 11, which is comprised of end plates 11a and coupling rods 11b (typically four in number), and a stress transfer assembly, which is comprised of stress rods 12, bearing plates 13, and coupling cylinders 14. The "active" elements are two sets of bellows 15, which provide static loading, and a pair of piezoelectric actuators 16, which provide dynamic loading. Each of these elements is described below, and for purposes of illustrating the natural resonance frequency of a typical SEM-compatible test machine 10, dimensions and other physical characteristics of these elements are also described.

Examples of suitable materials for test machine 10 are iron, titanium, and aluminum alloys for the structural elements and piezoelectric ceramic for the piezoelectric actuators 16. Table 1 lists physical properties of these materials. As used herein, the terms "steels", "aluminum", and "titanium" should be understood to include various alloys, especially those that exhibit increased strength. Table 2 lists the piezoelectric properties of the ceramic material used in the piezoelectric actuators 16.

Although several specific materials are identified herein as being suitable and are used as examples, other materials are also suitable. For example, iron alloys other than stainless steel may be used to provide higher stresses or a smaller test machine. Also, the dynamic stresses may be produced by means of other types of piezoelectric materials and ceramic compounds, such as barium titanate or lithium niobate. Furthermore, the dynamic stresses may be produced by means of a magnetostrictive material, such as Terfenol D or other similar rare earth compounds through appropriate modification of the dynamic loading actuators. In the case of a dynamic actuator made from magnetostrictive material, a set of rods with windings could be substituted for the piezoceramic stack. These rods would be placed between the retaining plate 13 a and the cylindrical coupler 14, parallel to the coupling rods 11b.

TABLE 1

| TEST FIXTURE MATERIAL | MODULUS OF ELASTICITY Y (Pa) | POISSON'S RATIO α | DENSITY ρ (Kg/m³) |
|---|---|---|---|
| Stainless Steel (304 or 316) | $194 \times 10^9$ | 0.265 | 7,970 |
| Titanium alloy | $117.6 \times 10^9$ | 0.300 | 4,540 |
| Aluminum alloy (6061) | $76.5 \times 10^9$ | 0.330 | 2,710 |
| Lead Zirconate Titanate Piezoceramic (Navy Type III) | $71 \times 10^9$ | 0.340 | 7,550 |

TABLE 2

| PIEZOELECTRIC PARAMETER | PARAMETER VALUE |
| --- | --- |
| Piezoelectric Strain Constant $d_{33}$ | $245 \times 10^{-12}$ (m/V) |
| Piezoelectric Stress Constant $g_{33}$ | $25.2 \times 10^{-3}$ (Vm/N) |
| Relative Dielectric Constant $\epsilon_{33}$ | 1100 |
| Loss Tangent @10 kV/in. tan $\delta$ | 0.01 |

Test machine 10 is symmetrical with respect to a "vertical" axis B—B. As a result, a stationary vibration node is located at a horizontal midpoint of test machine 10 along a horizonal axis A—A. During testing, the test specimen is placed at this node and is essentially stationary (no axial translation motions at the node) when observed by the SEM during dynamic excitation. The symmetry also serves as a point for mounting the test machine 10 on the SEM internal positioning stage. The mounting may be accomplished via a solid-material block (not shown) attached to the midpoints of the two lower coupling rods 11b. An example of a suitable material for such a mounting block is a neoprene rubber composition. Mounting test machine 10 to the SEM stage in this manner decouples the vibration of test machine 10 from the stage and from other parts of the SEM.

In the embodiment of this description, vertical symmetry is accomplished by placing identical components on either side of the stationary node. In other words, each end of the test machine 10 has identical components. Thus, test machine 10 has a pair of cylindrical couplers 14, a pair of piezoelectric actuators 16, and two sets of bellows 15, which perform the same functions at the two ends of test machine 10. However, symmetry could also be accomplished with one or more of these elements being implemented singly at one end rather than in pairs, with a compensating mass at the other end. For example, dynamic loading could be accomplished with a single piezoelectric actuator 16 at one end and a compensating mass at the other end.

Inner frame 11 is comprised of two end plates 11a connected by a set of four coupling rods 11b. End plates 11a and coupling rods 11b may be made of a steel, titanium, or aluminum alloy. Typically, end plates 11a are square or circular, but may be any convenient shape. Frame 11 serves as a means for containing stress rods 12, piezoelectric actuators 16, and coupling cylinders 14, as well as a surface against which bellows 15 may exert force.

Each end plate 11a has four circular holes sized to provide insert seats for coupling rods 11b, such that the two end plates 11a may be accurately oriented parallel to one another and separated by a distance set by the equal lengths of the coupling rods 11b. In the embodiment of FIG. 1, four coupling rods 11b are arranged in a square pattern near the peripheral boundaries of end plates 11a. Each coupling rod 11b is secured to the end plates 11a by screws that fix the end plates 11a to the ends of each rod 11b. A fifth hole in located in the center of each end plate 11a to allow a stress rod 12 to pass through it and to be attached to a bearing plate 13 and coupling cylinder 14.

The combined assembly—consisting of the inner frame 11, the bellows 15, the bearing plates 13, the stress rods 12, the piezoelectric actuators 16, cylindrical couplers 14, and the test specimen—forms a multi-element network of springs and masses that exhibits two predominant natural mechanical resonances. The highest natural resonance frequency is associated with the inner frame 11, governed mainly by the stiffness of the coupling rods 11b and the mass of end plates 11a, and is typically in the range of 5,000 to 10,000 Hz, above the range of interest for applying cyclic stresses. The second natural resonance is governed mainly by the stiffness of the test specimen and the combined mass of the cylindrical couplers 14, the piezoelectric actuators 16, and the stress rods 12. The dimensions of these various components, their material densities, and elastic constants (compliance versus stiffness) determine the natural resonance frequency and may be selected to achieve a resonance in the range of 1,000 to 4,000 Hz.

A static loading assembly at each end of test machine 10 has a bearing plate 13 and a stress rod 12, which are rigidly connected together. In the example of FIG. 2, the attachment of each stress rod 12 to its associated bearing plate 13 is accomplished by a threaded end of stress rod 12 and a nut outside bearing plate 13. Each stress rod 12 passes through a hole in an associated end plate 11b and extends horizontally inside inner frame 11 along the horizontal axis A—A of test machine 10. The stress rods 12 are preferably made of a steel or titanium alloy.

Dynamic loading is provided by a pair of dynamic actuators 16, assembled on stress rods 12 and located inside each end of inner frame 11. In the embodiment of FIGS. 1 and 2, the actuators 16 are implemented as piezoelectric stacks, each consisting of artificially polarized electrostrictive ceramic disks. Specifically, for each actuator 16, an even number, N, of piezoelectric ceramic disks, typically made from Navy Type III lead zirconate titanate material, are electroded on their plane surfaces and polarized along the disk thickness dimension. Each disk has a center hole to allow passage of a stress rod 12. In the embodiment of FIGS. 1 and 2, the disks are assembled onto stress rods 12 against a retainer plate 17a. A nut 17b is used to secure the retainer plate 17b. In this manner, each actuator 16 is placed in compression between the outer face of a cylindrical coupler 14 and the retainer plate 17a.

A typical piezoelectric actuator 16 might have 14 disks, with an assembled stack length of 0.742 inches. The disks are assembled in electrical parallel connection to provide relatively low-voltage mechanical series displacement actuation along the axis A—A. The maximum operating electric field within each disk is rated at approximately 20 volts/mil. For example, a 0.050 in. thick plate may be excited by a maximum voltage of 1,000 volts.

A set of bellows 15 is attached at each end of test machine 10, between an end plate 11a and a bearing plate 13. In the embodiment of FIG. 1, there are four bellows 15 at each end. However, a greater or fewer number could be used. Also, as stated above, only one set of bellows 15 at one end of test machine 10 could be used, with a compensating mass at the other end.

Each bellows 15 contains hydraulic fluid, and may be expanded by pressure in the fluid with a force proportional to the pressure. Alternatively, bellows 15 could be operated with pneumatic pressure. The hydraulic or pneumatic force is exerted against end plates 11a, thereby providing a compressive force on inner frame 11. An opposing force is also exerted against bearing plates 13. Due to the fixed attachment of stress rod 12 to bearing plates 13, and due to the coupling of the stress rod 12 to the cylindrical coupler 14 and test specimen, a resultant tensile force is applied to the test specimen. This results in a static loading on the test specimen. For two sets of four bellows 15, one set at each end of test machine 10, the static loading range of test machine 10 is within a range suitable for SEM test specimens, specifically, about 1,500 to 6,000 pounds of force for the typical specimen size specified above.

At each end of test machine 10, a cylindrical coupler 14 couples both a stress rod 12 and a piezoelectric actuator 16 to one end of the test specimen. In other words, the test specimen is positioned between the cylindrical couplers 14 and receives static and dynamic loading at both ends. For this purpose, each cylindrical coupler 14 may be attached to a stress rod 12 in any manner that transfers static loading applied by bellows 15 to stress rod 12, and may be attached to piezoelectric actuator 16 in any manner that transfers dynamic loading applied by the actuator 16. As explained above, in the embodiment of FIG. 1, each cylindrical coupler 14 is attached to a stress rod 12. Static loading is transferred through the stress rods 12 to the cylindrical couplers 14. Also, each stress rod 12 holds a piezoelectric actuator 16, which is compressed between a retainer plate 17a and a cylindrical coupler 14 by means of a locking nut 17b, thereby causing a constrained attachment of the cylindrical coupler 14 to the actuator 16. In this manner, the dynamic loading provided by actuators 16 is transferred to cylindrical couplers 14. However, it should be understood that the mechanics of attaching components so as to accomplish the loading transfer to cylindrical couplers 14 could be accomplished in many different ways.

Each cylindrical coupler 14 consists of a right circular cylinder, having a base slightly larger than the piezoelectric actuators 16. For example, a cylindrical coupler 14 might be 0.100 inch larger in diameter than the piezoelectric actuator 16. A typical length might be 1.50 inch.

Each cylindrical coupler 14 has an inner face in which the ends of the test specimen are gripped. A design objective of the cylindrical couplers 14 is to minimize the mass of each coupler 14 to maximize the stress transferred from its piezoelectric actuator 16 to the test specimen, as well as to achieve the desired natural resonance frequency in the range of 1,000 to 4,000 Hz. Thus, the cylindrical couplers 14 are preferably made of a titanium alloy for light weight and high strength. Alternatively, couplers 14 may be made of either an aluminum alloy or a steel alloy with weight-reducing drill holes introduced where appropriate.

FIG. 2 illustrates one example of how a test specimen is secured in test machine 10 for testing. The specimen is generally in the shape of a strip approximately 1 inch long and ½ inch wide. The center of this strip is flat with a thickness of about ⅛ inch. At each end, the specimen is gradually flared to a greater thickness. Each end of the test specimen is placed in a wedge-grip formed by wedge retainers 18 in a face of a cylindrical coupler 14. Wedge retainers 18 holds the specimen in place under static tensile loading. Pins or other suitable mechanisms (not shown) may be used to secure the specimen in cylindrical coupler 14.

Control System for SEM-Compatible Test Machine

Figure 3:
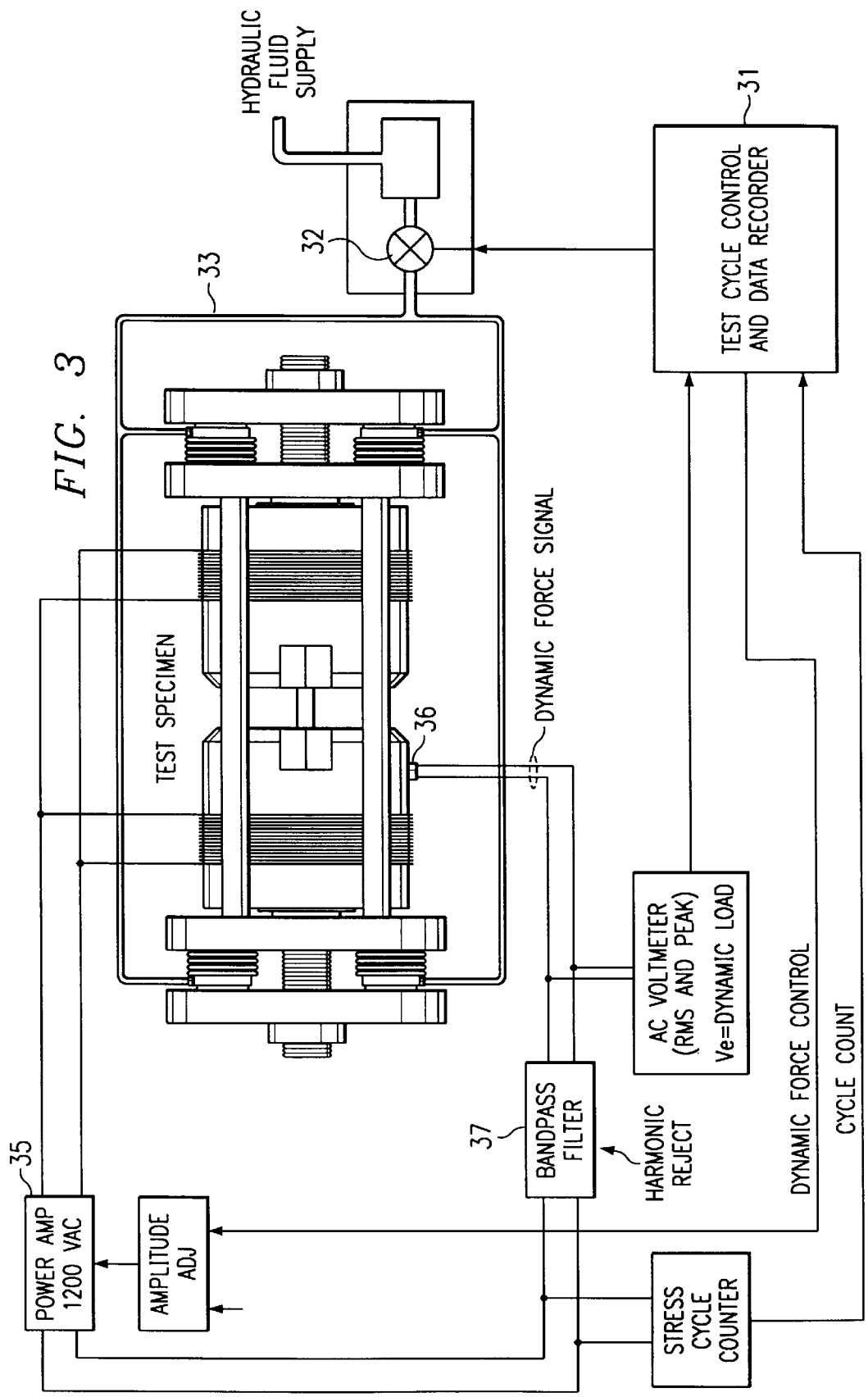
FIG. 3 illustrates a control system for the test machine of FIG. 1.

FIG. 3 illustrates a control system for the SEM-compatible test machine 10 of FIGS. 1 and 2. A feature of the invention is that dynamic and static loading may be independently controlled. These forces may be maintained at preset values independent of the cyclic loading frequency.

As explained above, test machine 10 provides tensile static loading in combination with cyclic dynamic loading. Static loading on the specimen may be applied separately from dynamic loading, and it may be adjusted during quiescent periods of the test so that any fatigue defect conditions in the specimen can be microscopically examined under varied strain. Stroboscopic SEM techniques can also be devised to observe the specimen during testing, by capturing microscopic images at selected time-slice intervals.

A computer 31 may be suitably programmed to handle control inputs for regulating both the static and dynamic stresses in the test specimen, as well as to record test results. Computer 31 may be any general purpose personal or desktop computer, such as are commercially available.

Static loading is controlled by adjusting the hydraulic pressure via either a manually controlled or computer controlled valve 32. Hydraulic fluid lines 33 carry hydraulic fluid to and from bellows 15.

The dynamic loading is produced by electrically activating the piezoelectric actuators 16 with an AC voltage, causing them to vibrate. Their oscillatory motion is transferred to the test specimen by means of the cylindrical couplers 14. A power amplifier 35 drives the two piezoelectric actuators 16 connected electrically in parallel.

The dynamic loading is feedback controlled. Because the operating frequency of test machine 10 is a function of the natural resonance of the specimen in combination with the mass of the cylindrical couplers 14, the operating frequency will depend upon the specific test specimen geometry and can be expected to change with the temperature and fatigue status of the specimen. Variations in resonance can present a problem in maintaining uniform stress excitation in the specimen during the fatigue testing cycle and could lead to inaccurate results in predicting the specimen fatigue tolerance. For this reason, a vibration sensor 36 is used to sense the dynamic resonance frequency of the fixture during testing. This arrangement ensures that the fatigue-inducing stresses in the specimen, controlled primarily by the vibrational energy of the fixture, will be maintained constant by tracking the resonance frequency throughout the test period.

By means of vibration sensor 36, a signal directly proportional to the cyclic loading force on the specimen and at the frequency of oscillation of test machine 10 is obtained. This signal is filtered by bandpass filter 37 to remove any harmonic distortion and is fed to the power amplifier 35, which drives the piezoelectric actuators 16. The output of the power amplifier 35 is adjustable by computer 31 to produce the desired amplitude of the sinusoidal cyclic stress applied to the specimen, independently of the machine resonance frequency. Feedback control of the power amplifier 35 ensures that the electrical drive signal is at the mechanical resonance of test machine 10 thereby tracking any changes in resonance that may occur due to changes in temperature or specimen physical properties.

The static loading on the test specimen is controlled at a preset value by sensing the hydraulic fluid pressure in the bellows pressurizing system and regulating the pressure by valve 32. Valve 32 may be controlled by computer 31.

SEM-Compatible Test Machine With Piezoelectric Static and Dynamic Loading

Figure 4:
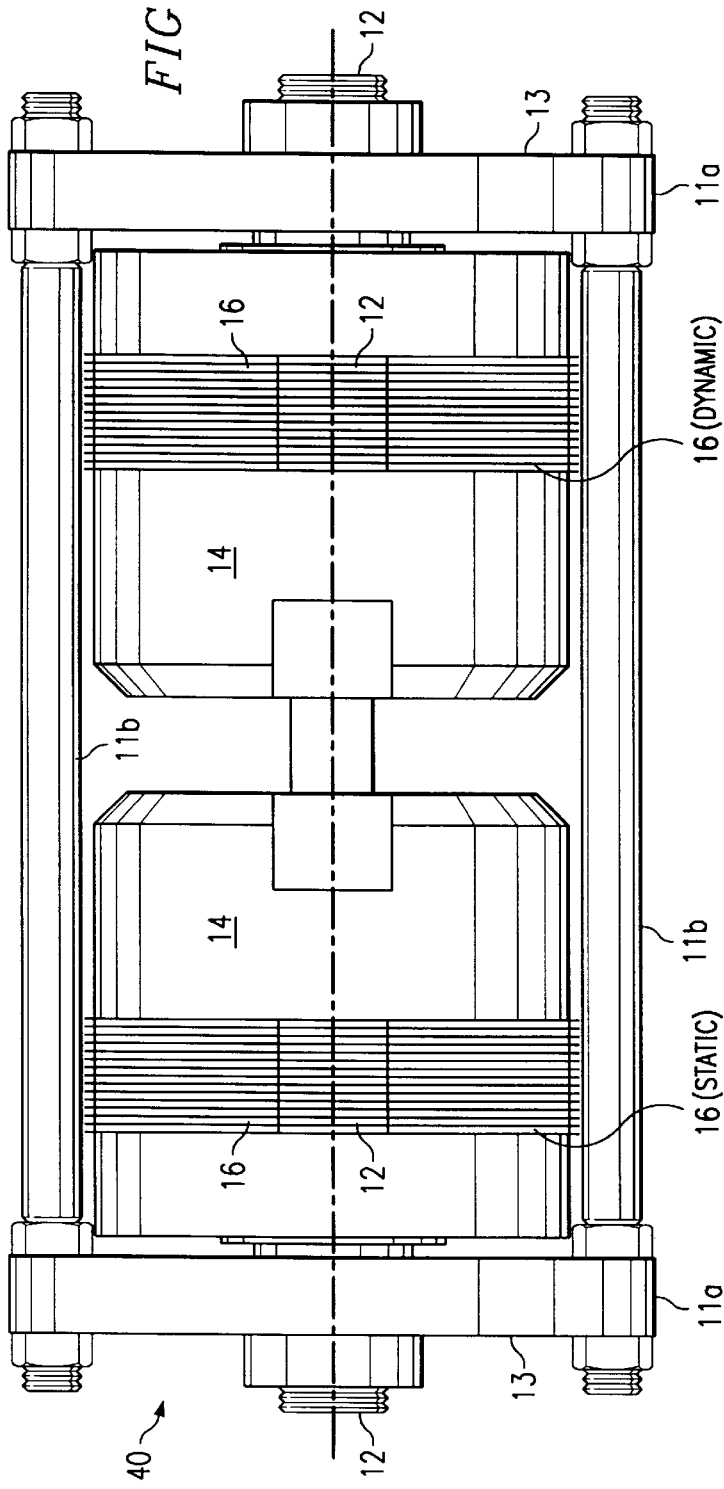
FIG. 4 illustrates a modified version of the SEM-compatible test machine.

FIG. 4 illustrates another SEM-compatible test machine 40, which is a modified version of the SEM-compatible test machine 10. In FIG. 4, the static loading is accomplished by one of the piezoelectric actuators 16, rather than with bellows 15 and bearing plates 13.

As in FIGS. 1 and 2, the piezoelectric actuators are implemented with piezoelectric actuators 16. However, for test machine 40, the control system of FIG. 3 would be modified so as to provide a DC voltage from a DC power supply (not shown) to one piezoelectric actuator 16, and an AC voltage to the other. No hydraulic system or bellows 15 would be used. The piezoelectric actuator 16 to which the DC voltage is applied could be excited electrically such that it shrinks to provide a tensile static load on the test specimen, or, with appropriate attachment of stress rod 12 and bearing plate 13, such that it expands to provide a compressive static load.

Resonance of Test Machine

Cyclic vibrations in the kilohertz frequency range are achieved by operating test machine 10 at the natural resonance frequency of the test machine 10. This resonance is a function of the physical characteristics of the test specimen as well as of the test machine 10. As stated above, a typical range of operating frequencies is 1,000 to 4,000 Hz.

Figure 5:
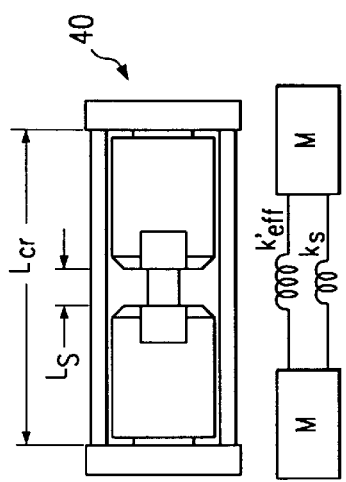
FIG. 5 illustrates the calculation of the cyclic stress rate provided by the test machine of FIG. 4.

FIG. 5 illustrates how the natural resonance of test machine 40 can be calculated by modeling its various spring and mass components. Similar calculations would be made for test machine 10, but with the added spring and mass representations of the bellows 15 and bearing plates 13. However, the calculations are easily modified to calculate resonance with these elements included.

For test machine 40, each value of M is one-half the total mass of test machine 10 minus the mass of the coupling rods 11b and the mass of the specimen. Some characteristics of test machine 40, used in determining its resonance frequency are:

End plates (2 each)
  Diameter 3.75 inches ($9.525 \times 10^{-2}$ m)
  Thickness 0.375 inch ($9.525 \times 10^{-3}$ m)
  Volume—3.857 in$^3$
  Stainless Steel—1.111 lb
  Aluminum—0.378 lb
Coupling rods (four each)
  Length 10.50 inch (0.2667 m)
  Diameter 0.400 inch ($1.016 \times 10^{-2}$ m)
  Volume—$1.111 \times 10^{-4}$
  Stainless Steel—1.952 lb
  Aluminum—0.664 lb.
Stress rods (two each)
  Volume—0.477 cubic inches.
  Stainless steel—0.138 pound
  Aluminum—0.0468 pound
Piezoelectric stacks (two each)
  Number of disks=N (even number)=42
  Disk diameter—3.000 in. ($7.62 \times 10^{-2}$ m)
  Disk hole diameter 1.25
  Disk thickness 0.050 in ($1.270 \times 10^{-3}$ m)
  Disk bonding interface 0.003 in ($7.62 \times 10^{-5}$ m)
  Stack volume—15.277 in$^3$
  Stack piezoceramic—4.167 lb
Cylindrical couplers (two each)
  Volume—6.508 in$^3$
  Stainless steel—1.874 lb
  Aluminum—0.637 lb Consistent with the above examples of dimensions of the various components of test machine 40, its total weight is 16.53 pounds when made of stainless steel or 11.12 pounds when made of an aluminum alloy. For purposes of determining the principle mechanical resonance of the test fixture, a relatively stiff cylinder specimen made of stainless steel is assumed. The diameter of this test specimen is 0.25 inch and its length is 0.75 inch.

The fundamental resonance of the specimen and the two symmetrically attached and equal masses, each composed of a cylindrical coupler 14, a piezoelectric actuator 16, a retainer plate 17a, and a stress rod 12, is:

$$f_{rs} = \frac{1}{2\pi} \sqrt{\frac{2Y_s A_s}{ML_s}}$$
$$= 2265 \text{ Hz},$$

, neglecting the distributed mass of the specimen and the distributed masses of the remaining end attachments and inner frame, where:

$Y_s = 194 \times 10^9$ Pa
$A_s = 3.17 \times 10^{-5}$ m$^2$
$L_s = 1.91 \times 10^{-2}$ m
$M = 3.18$ kg This estimate of the resonance of test machine 10 indicates that it will provide dynamic loading in the desired frequency range. Further, by repeating this frequency calculation using the material properties of titanium in the specimen and in the test fixture, the natural resonance of the machine was found to be 2300 Hz.

Thus, in order to obtain a lighter weight test fixture, titanium construction may be preferred. A test machine whose fixture components are made of aluminum and operating with a stainless steel or titanium specimen, might be preferred to achieve an even lighter weight machine that has approximately the same or a higher natural resonance frequency.

The above analysis also demonstrates that the test specimen will have a significant influence on the resonance frequency. A test specimen having a higher modulus or a larger cross-section will increase the frequency.

Laboratory Test Machine

Figure 6:
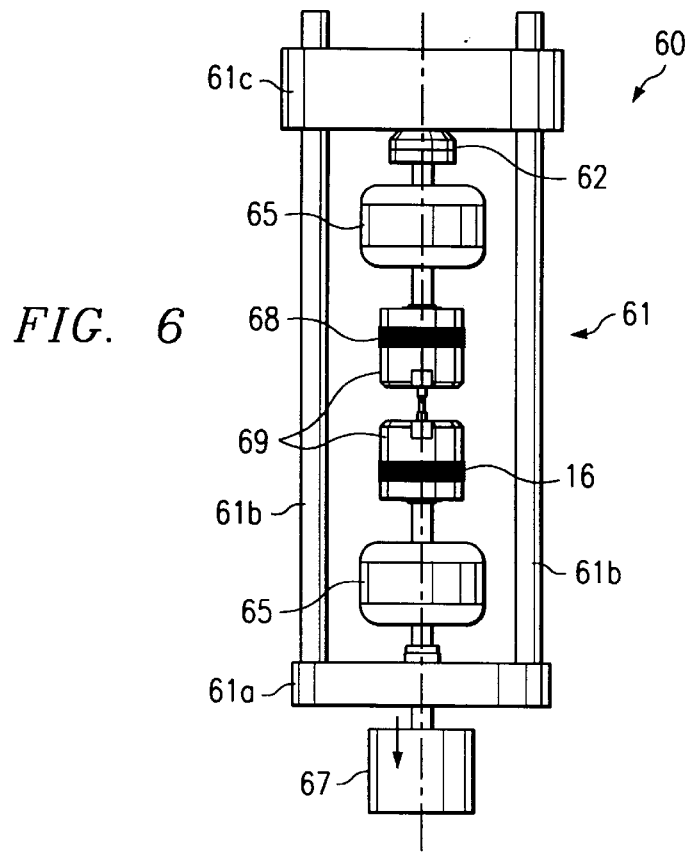
FIG. 6 illustrates a laboratory test machine in accordance with the invention.

FIG. 6 illustrates a laboratory test machine 60, which is an alternative embodiment of the invention. It applies dynamic loading to a test specimen in a manner similar to SEM-compatible test machine 10, using a pair of piezoelectric actuators 68. Essentially, actuators 68 and couplers 69 are the same as those described above for test machine 10. However, as explained below, test machine 40 applies static force electromechanically with an outer loading frame rather than hydraulically.

Outer loading frame 61 is comprised of a base 61a, from which at least two risers 61b extend vertically. A cross-bar 61c is attached between risers 61b.

A first stress rod 64 is attached to cross bar 61c at one end and extends vertically down from cross bar 61c. A second stress rod 64 extends upwardly from base 61a and is attached to a gear box of a servo-electric motor 67. The motor 67 is used to pull the lower stress rod 64 in the direction indicated by the arrow, thereby subjecting the specimen attached between stress rods 64 to tensile loading. Alternatively, the motor 67 could be used to push the lower stress rod, thereby subjecting the specimen to compressive loading.

Piezoelectric actuators 68 and cylindrical couplers 69 are mounted on stress rod 64 in a manner similar to that described above for test machine 10. Also, the test specimen is mounted between the cylindrical couplers 69 as described above. Thus, the tensile loading of stress bar 64 subjects the test specimen to tensile loading.

Dynamic loading of the test specimen is accomplished with piezoelectric actuators 68, as described above in connection with test machine 10. Because the laboratory test machine 50 is not required to fit within a SEM vacuum chamber, certain modifications, such as the enlargement of piezoelectric actuators 16, are possible in order to achieve higher dynamic loading on larger test specimens without reducing the resonance frequency below the operating range of interest.

A pair of isolators 65, typically made of stainless steel, one between base 61a and piezoelectric actuator 69 and the other between cross-bar 61c and the other piezoelectric actuator 68, isolate the oscillatory motion of the test machine 60 from the electromechanical components of the system. A load cell 62 is used to measure the static loading applied to the test specimen.

High-cycle Fatigue Test Sequence

Figure 7:
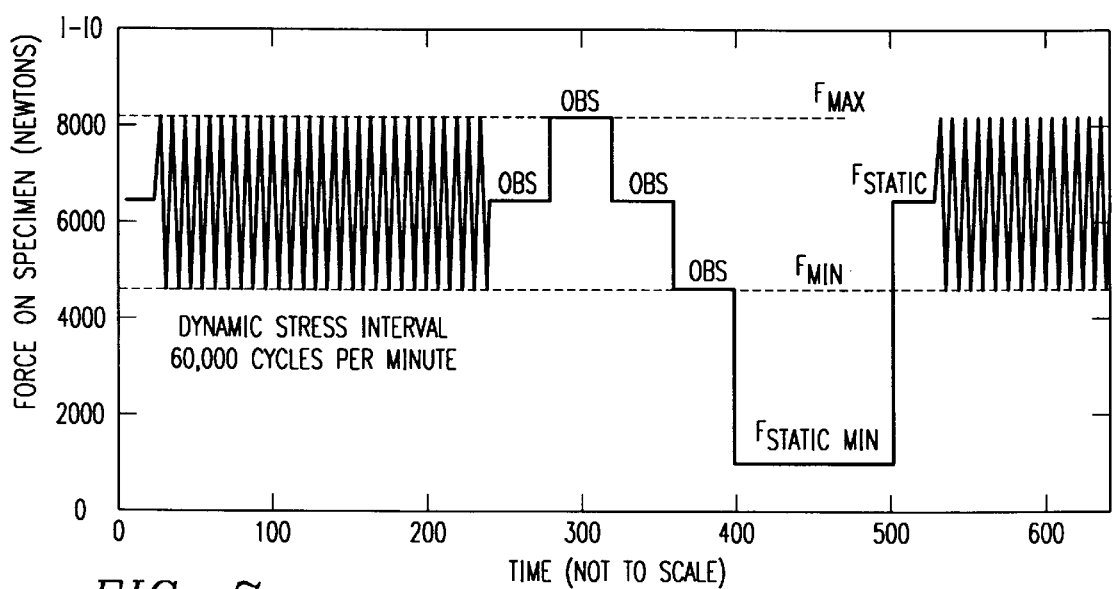
FIG. 7 illustrates a typical high-cycle fatigue test sequence in accordance with the invention.

FIG. 7 illustrates a typical stress/strain test sequence used with test machine 10, 40, or 60. The dynamic stresses are superimposed on a static stress applied to the test specimen. The dynamic loading is applied for a preset number of oscillatory stress cycles. This dynamic loading is stopped after the preset number of cycles so as to permit the specimen to be inspected microscopically at the static stress condition (or at some other static load). After inspection of the specimen, the testing sequence is repeated. The lapse between dynamic loading sequences may be a preset time of quiescent static stress.

Other Embodiments

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A test machine for applying static and dynamic stress loading to a test specimen, comprising:
    an inner frame being generally in the shape of a hollow tube and having opposing end plates along a horizontal axis;
    two sets of bellows, each of said bellows having an axis of motion parallel to said horizontal axis, and each of said bellows having an inner end and an outer end, said inner ends of one set of bellows attached to one of said end plates and said inner ends of the other set of bellows attached to the other of said end plates;
    a pair of bearing plates, each of said bearing plates attached to said outer ends of each said set of bellows, such that each said set of bellows is located between an end plate and a bearing plate;
    two stress rods, each one of said stress rods attached to one of said bearing plates and extending inwardly through an associated end plate;
    a pair of dynamic actuators, each one of said actuators being attached to one of said stress rods; and
    a pair of cylindrical couplers, each of said cylindrical couplers having an inner face with means for attaching one end of said test specimen, and each of said cylindrical couplers being attached to a stress rod and an actuator such that force applied to said stress rod by said bellows is transferred to said specimen and such that force provided by said actuators on said stress rods is transferred to said specimen;
    wherein said stress rods, said cylindrical couplers, and said actuators provide a predetermined natural resonance when said test machine is in operation with said test specimen.

2. The test machine of claim 1 wherein said stress rods, said actuators, said cylindrical couplers, and said test specimen form symmetrically opposing elements of said test machine inside said inner frame thereby providing a stationary vibration node of said test machine at the midpoint of said test specimen.

3. The test machine of claim 1, wherein said inner frame is comprised of a set of coupling rods attached between said end plates.

4. The test machine of claim 1, wherein said test machine has an overall size that is sufficiently small to fit inside the vacuum chamber of an SEM microscope.

5. The test machine of claim 1, wherein said actuators are made from piezoelectric material.

6. The test machine of claim 1, wherein said actuators are made from magnetostrictive material.

7. The test machine of claim 1, wherein the effective masses and compliances of said stress rods, cylindrical couplers, actuators, and test specimen exhibit a natural resonance, in a frequency range in the order of 1000 Hz and above, for dynamically loading said test specimen.

8. A test machine for applying static and dynamic stress loading to a test specimen, comprising:
    an inner frame being generally in the shape of a hollow tube and having opposing end plates along a horizontal axis;
    a pair of dynamic actuators, one of said actuators placed inside each end of said inner frame, one of said actuators having means for receiving a constant applied voltage and the other of said actuators having means for receiving an alternating applied voltage; and
    a pair of cylindrical couplers, one inside each end of said inner frame, each of said cylindrical couplers having an inner face with means for attaching one end of said test specimen, and each of said cylindrical couplers being attached to an actuator such that forces provided by said actuators are transferred to said specimen;
    wherein said cylindrical couplers and said actuators provide a predetermined natural resonance when said test machine is in operation with said test specimen.

9. The test machine of claim 8, wherein said actuators and said cylindrical couplers form symmetrically opposed vibrational elements of said test machine inside said inner frame thereby providing a stationary vibration node of said test machine at the midpoint of said test specimen.

10. The test machine of claim 8, wherein said inner frame is comprised of a set of coupling rods attached between said end plates.

11. The test machine of claim 8, wherein said test machine has a length and height sufficiently small to fit inside the vacuum chamber of an SEM microscope.

12. The test machine of claim 8, further comprising two stress rods, one each extending inwardly inside said inner frame and wherein each of said cylindrical couplers is attached to an associated stress rod such that force applied to said stress rod is transferred to said cylindrical coupler and to said specimen.

13. The test machine of claim 8, wherein said actuators are comprised of piezoelectric material.

14. The test machine of claim 8, wherein said actuators are comprised of magnetostrictive material.

15. The test machine of claim 8, wherein the effective masses and compliances of said cylindrical couplers, said actuators, and said test specimen exhibit a natural resonance, in a frequency range in the order of 1000 Hz and above, for dynamically loading said test specimen.

16. A test machine for providing static and dynamic stress loading to a test specimen, comprising:
    an outer frame having a base and an upper member supported above said base;
    two stress rods, one extending upward from said base and one extending downward from said upper member;
    a pair of dynamic actuators, one each attached to an associated stress rod;
    a pair of cylindrical couplers, one each attached to an associated stress rod, each of said cylindrical couplers having an inner face with means for attaching one end of said test specimen between said cylindrical couplers, and each of said cylindrical couplers being attached to an associated stress rod and to an associated actuator such that force applied to said stress rod is transferred to said specimen and such that force provided by said actuator is transferred to said specimen;

wherein said stress rods, said cylindrical couplers, and said actuators provide a predetermined natural resonance when said test machine is in operation with said test specimen.

17. The test machine of claim 16, wherein said actuators are comprised of piezoelectric material.

18. The test machine of claim 16, wherein said actuators are comprised of magnetostrictive material.

19. The test machine of claim 16, further comprising a pair of isolators, one placed between said upper member and an associated actuator and another placed between said base and an associated actuator.

20. The test machine of claim 16, wherein the effective masses and compliances of said stress rods, cylindrical couplers, actuators, and test specimen exhibit a natural resonance, in a frequency range in the order of 1000 Hz and above, for dynamically loading said test specimen.

21. A method of applying static and dynamic stress loading to a test specimen, comprising the steps of:

attaching a test specimen to an inner face of each one of a pair of cylindrical couplers;

attaching a dynamic actuator to an outer face of each said cylindrical couplers thereby providing a pair of actuators;

attaching a stress rod to each of said cylindrical couplers, wherein said couplers, said actuators, and said stress rods have a desired natural resonance frequency;

applying a static load to said stress rod; and applying an alternating voltage to at least one of said dynamic actuators thereby causing said actuator to oscillate at a frequency substantially the same as said natural resonance frequency.

22. The method of claim 21, wherein said cylindrical couplers, said actuators, said stress rods, and said test specimen are placed inside a frame, and said step of applying a static load is performed with force applied to end plates of said frame.

23. The method of claim 21, wherein said step of applying a static load is performed by placing said stress rods in tension.

24. The method of claim 21, wherein said step of applying a static load is performed by applying a constant voltage to one of said actuators.

25. The method of claim 21, wherein said step of applying an alternating voltage is controlled by a feedback signal from said actuator.

26. The method of claim 21, wherein said steps of applying static stress loading and applying dynamic stress loading are independently controlled.

27. The method machine of claim 1, wherein the effective masses and compliances of said stress rods, cylindrical couplers, actuators, and test specimen exhibit a natural resonance frequency, in a frequency range in the order of 1000 Hz and above, for dynamically loading said test specimen.

* * * * *